United States Patent
Alyassin et al.

(12)

(10) Patent No.: US 6,611,575 B1
(45) Date of Patent: Aug. 26, 2003

(54) METHOD AND SYSTEM FOR HIGH RESOLUTION 3D VISUALIZATION OF MAMMOGRAPHY IMAGES

(75) Inventors: Abdalmajeid Musa Alyassin, Niskayuna, NY (US); Jeffrey Wayne Eberhard, Albany, NY (US); Bernhard Erich Hermann Claus, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/682,156

(22) Filed: Jul. 27, 2001

(51) Int. Cl.[7] .................................................. A61B 6/04
(52) U.S. Cl. ............................ 378/37; 378/197; 378/22
(58) Field of Search .......................... 378/37, 197, 22, 378/4, 21, 23; 382/131, 132

(56) References Cited

U.S. PATENT DOCUMENTS

| | | | |
|---|---|---|---|
| 4,482,958 A | | 11/1984 | Nakayama et al. ......... 364/414 |
| 4,894,776 A | * | 1/1990 | Dekel .................... 364/413.13 |
| 5,872,828 A | | 2/1999 | Niklason et al. ............... 378/23 |
| 5,934,288 A | | 8/1999 | Avila et al. ................. 128/916 |
| 6,081,577 A | * | 6/2000 | Webber ....................... 378/23 |
| 6,102,861 A | | 8/2000 | Avila et al. ................. 600/443 |
| 6,196,715 B1 | * | 3/2001 | Nambu et al. ............... 378/197 |
| 6,256,370 B1 | * | 7/2001 | Yavuz .......................... 378/22 |

FOREIGN PATENT DOCUMENTS

WO 00/68863 5/2000

OTHER PUBLICATIONS

Patent Application RD–26,827, "Apparatus and Method For Obtaining X–Ray Tomosynthesis Data For Mammography", Ralph Allen Hewes and Mehmet Yavuz, Ser. No. 09/409,889, filed Oct. 1, 1999.

* cited by examiner

Primary Examiner—Drew A. Dunn
Assistant Examiner—Irakli Kiknadze
(74) Attorney, Agent, or Firm—Jean K. Testa; Patrick K. Patnode (57) ABSTRACT

A method and system are provided for generating at least one three-dimensional image of an object volume. The three-dimensional image is generated by applying a selected three-dimensional (3D) visualization technique on the tomosynthesis data. The tomosynthesis data of the object volume is obtained by an imaging device for irradiating the volume with radiation at a plurality of radiating positions. The imaging device generates a plurality of spaced-apart planar images through the object volume from a plurality of projection radiographs which are derived by detecting radiation at the plurality of radiating positions.

13 Claims, 5 Drawing Sheets

METHOD AND SYSTEM FOR HIGH RESOLUTION 3D VISUALIZATION OF MAMMOGRAPHY IMAGES

FEDERAL RESEARCH STATEMENT

[The U.S. Government may have certain rights in this invention pursuant to contract number MDA 905-00-1-0041 awarded by the United States Navy.]

BACKGROUND OF INVENTION

This invention relates generally to mammography, and more particularly, to a method and system for readily generating three-dimensional images based on tomosynthesis data derived from x-ray examination of a patient's breasts.

Figure 1:
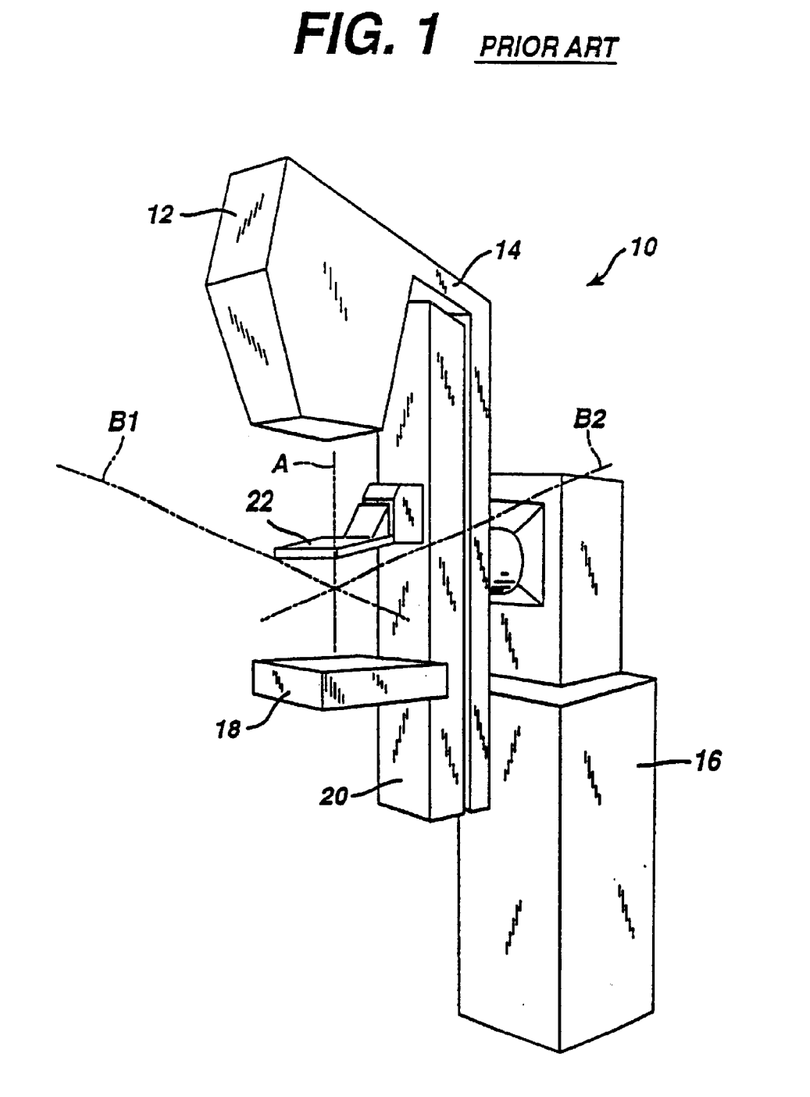
FIG. 1 is a perspective view of a prior art x-ray mammography machine.

Mammography is a low-dose x-ray procedure that creates one or more images of a patient's breasts desirable for detection of early stages of cancer. FIG. 1 illustrates one example of a prior art mammography machine 10. Mammography machine 10 generally includes an x-ray tube 12 attached to an arm 14, which arm 14 is pivotally attached to a support 16, and a film plate or digital detector 18 attached to an arm 20, which arm 20 is also pivotally attached to support 16. X-ray tube 12 and arm 14, and digital detector 18 and arm 20, are counterbalanced so that x-ray tube 12 and digital detector 18 may be easily manually pivoted, upwardly and downwardly, and locked in position at different angular orientations.

A typical mammography procedure takes approximately thirty minutes. The procedure generally includes obtaining two images of each of the patient's breasts, one from above and one from the side. For example, separate images are obtained of each of the patient's breasts with x-ray tube 12 and digital detector 18 disposed in a vertically orientated arrangement along axis A (i.e., cranio-caudal) as shown in FIG. 1. In addition, separate images are obtained of each of the patient's breasts with x-ray tube 12 and digital detector 18 oriented at an angle, e.g., along axis B1 (i.e., mediolateral oblique) for one of the patient's breasts, and along axis B2 for the patient's other breast.

During the procedure, the patient's breast is compressed between a compression paddle 22, e.g., a piece of radiographically transparent plastic, and digital detector cover 18 to flatten the breast, thereby decreasing the thickness and spreading the breast tissue, making the breast easier to be imaged. In obtaining the images, either from above or from the side, x-ray tube 12 is generally aligned perpendicular or normal to film plate or digital detector 18. A physician or radiologist then reviews the images of the breast, i.e., mammograms, to identify any breast cancer.

While the above described procedure is one of the best methods of detecting early forms of breast cancer, it is still possible for the breast cancer to be missed by a physician or radiologist reviewing the mammograms. For example, breast cancer may be missed by being obscured by radiographically dense, fibroglandular breast tissue, which is superimposed on the structures of interest in the mammogram.

Tomosynthesis breast imaging, in which a plurality of images or projection radiographs are acquired as the x-ray source is moved in an arc relative to the stationary breast and a stationary digital detector, has been studied in an effort to improve early detection of breast cancer. By shifting, scaling, and adding the plurality of projection radiographs, it is possible to reconstruct any plane in the breast being imaged that is parallel to the detector, thereby "removing" superimposed tissue from the structures of interest.

Visualizing micro-calcifications and masses, cysts, and other diagnostically relevant structures of the breast in a series of two-dimensional (2D) planes acquired from tomosynthesis breast imaging provides important diagnostic information. However, the volume of data is generally large and contains a considerable range of data content. Thus, radiologists essentially attempt to conceptually reconstruct these planes into a 3D structure by viewing approximately, for example, 60–80 images (usually 10 images for each cm of compressed breast thickness and each typically has a 2304×1800 matrix size) which makes this task difficult and time-consuming.

Therefore, there is a need for a method and system to visualize the data in 3D (e.g. Volume Rendering) to readily generate three-dimensional images of a patient's breast in order to aid in diagnosis of abnormal breast structures.

SUMMARY OF INVENTION

A method and system are provided for generating at least one three-dimensional image of an object volume. The three-dimensional image is generated by applying a selected 3D visualization technique (Volume Rendering, Surface Rendering, or the combination of the two) on the tomosynthesis data. The tomosynthesis data of the object volume is obtained by applying a suitable reconstruction algorithm to a set of projection radiographs acquired by an imaging device for irradiating the volume with radiation at a plurality of radiating positions. The imaging device generates a plurality of spaced-apart planar images through the object volume by executing a suitable reconstruction algorithm. This reconstruction algorithm is based on the projection radiographs derived by detecting radiation at the plurality of radiating positions.

BRIEF DESCRIPTION OF DRAWINGS

The features and advantages of the present invention will become apparent from the following detailed description of the invention when read with the accompanying drawings in which.

DETAILED DESCRIPTION

Figure 2:
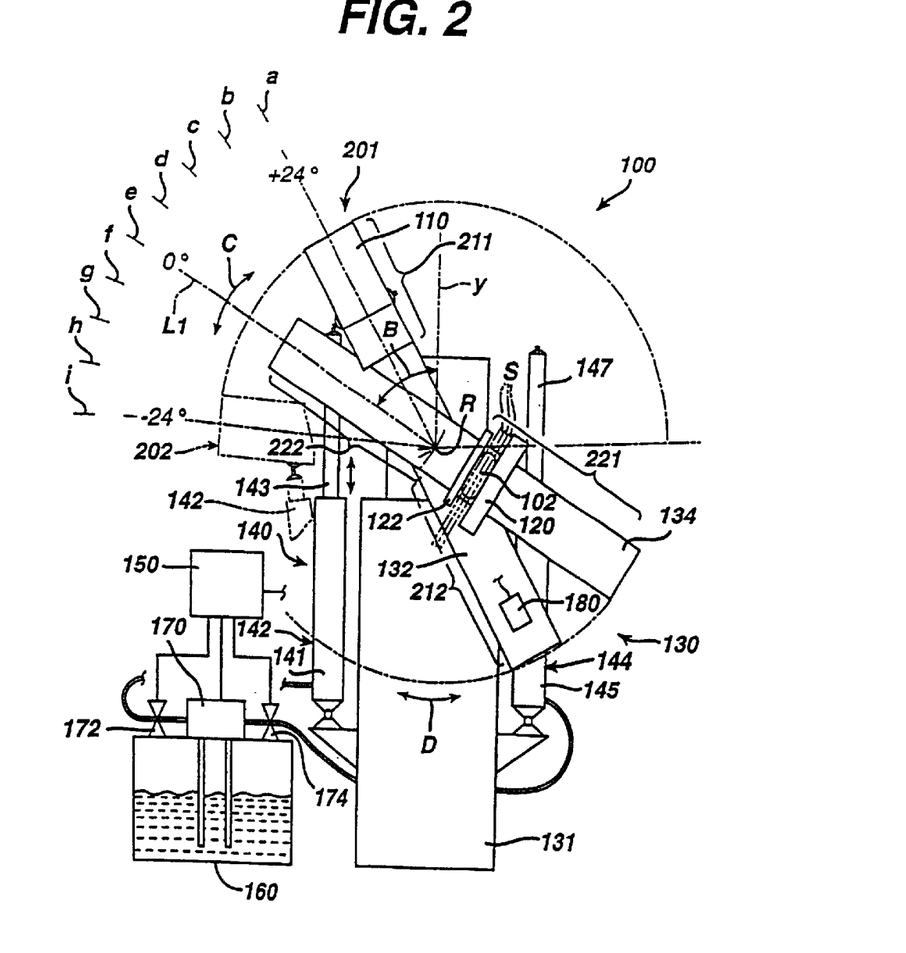
FIG. 2 is a diagrammatic, front elevational view of an apparatus for obtaining projection radiographs used for generating tomosynthesis data of a patient's breast to which embodiments of the present invention are applicable.
Figure 3:
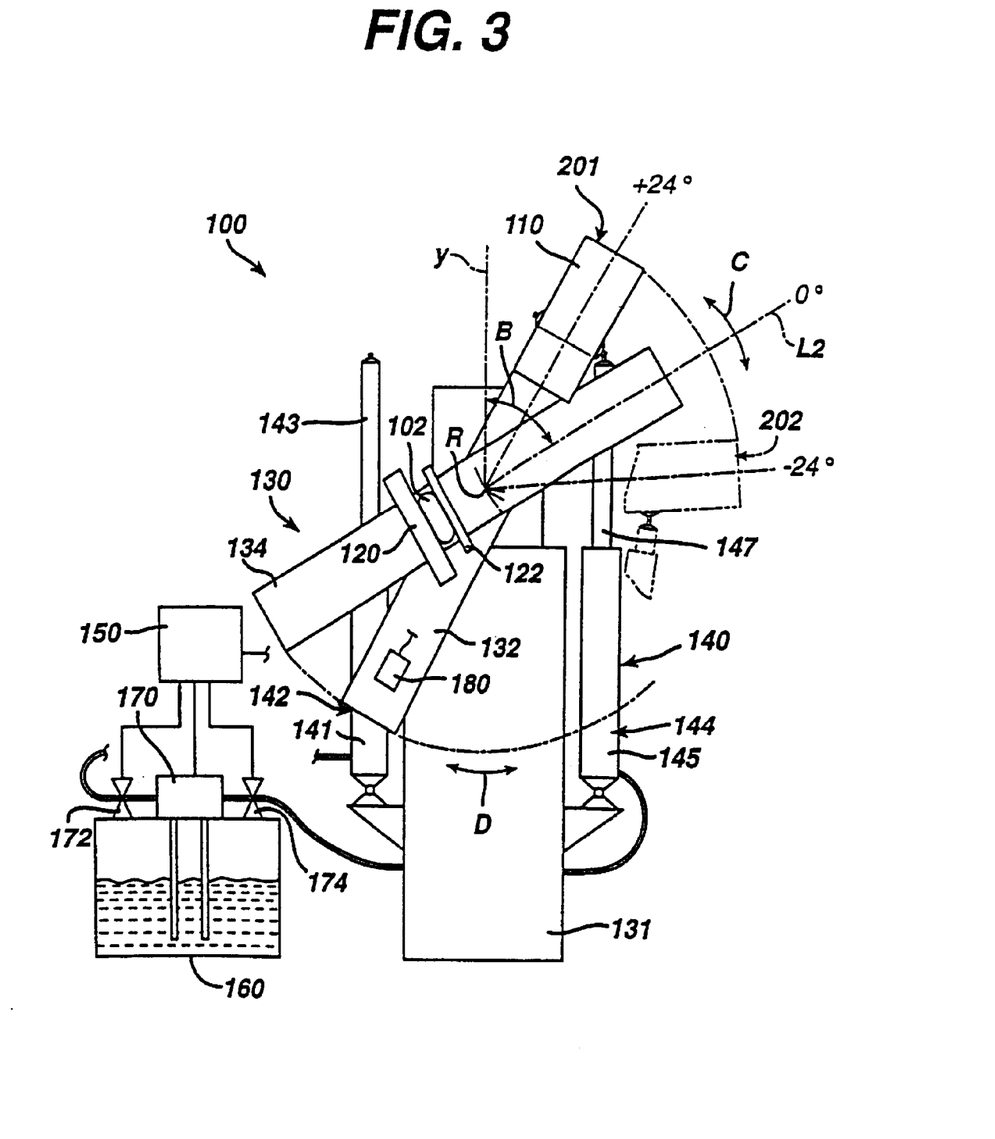
FIG. 3 is a diagrammatic, front elevational view of the apparatus, shown in FIG. 2, configured for obtaining projection radiographs used for generating tomosynthesis data of the patient's other breast.

An apparatus 100 for obtaining x-ray projection radiographs used for generating tomosynthesis data of an object 102 such as a patient's breast for early detection of cancer is illustrated in FIGS. 2 and 3. In this exemplary embodiment, the apparatus operates in conjunction with gravity to smoothly move a radiation source through a plurality of positions relative to a radiation detector and the patient's breast to obtain a plurality of projection radiograph of the patient's breast which can be processed for examination by a physician or radiologist.

The actuator is operable to control movement of the radiation source so that the radiation source substantially stops at the plurality of positions and is operable to smoothly transition the radiation source between the plurality of positions. Desirably, the acceleration of the radiation source varies in general smoothly, e.g. sinusoidally, over time.

Alternatively, an arm having a first end portion is attached to the radiation source and a second end portion is pivotally attached to a support so that the radiation source is movable along an arc. A hydraulic system operably connectable to the arm controllably allows the radiation source to move under the influence of gravity from at least one elevated position to at least one lower position relative to the radiation detector, wherein radiation emitted from the radiation source at a plurality of positions between the at least one elevated position and the at least one lower position and passing through the object is detectable by the radiation detector. As used herein, "under the influence of gravity" and the like refers to gravity being the motive force for transitioning the x-ray source from one position to a next sequential position as the source is moved to obtained the desired tomosynthesis data. Further, as used herein, "operably connected" and the like refers to a coupling of components together to enable the components to provide a desired operation or movement; examples include, but are not limited to, mechanical coupling by means of fasteners (such as cotter pin couplings, spring release latches, and the like) that provide a detachable coupling between component parts.

A method for obtaining tomosynthesis data of an object comprises the steps of positioning a radiation source in an elevated position with the object disposed between the radiation source and a radiation detector, irradiating the object with radiation at a plurality of radiating positions as the radiation source is allowed to move under the influence of gravity from an elevated position to a lower position, and detecting radiation passing through the object at the plurality of positions with the radiation detector. The method further includes the step of generating, from projection radiographs derived by detecting radiation passing through the object at each of the plurality of positions, a plurality of spaced-apart planar images through the object.

Such an apparatus is simpler and more robust than, for example, a mammography machine with one or more servomotors, which are used to physically move and position the x-ray source relative to the digital detector. Such a motorized system imparts thrusting or jolting motions to the machine that affects the ability to maintain the detector and the patient's breast in a stationary or fixed position throughout the procedure. Advantageously, the apparatus limits abrupt thrusting or jolting motions throughout the apparatus, so that the detector and the patient's breast is better maintained in a stationary position throughout the procedure.

Exemplary apparatus 100 includes an x-ray source 110, a detector 120, and an actuator 130 for controllably allowing x-ray source 110 to move under the influence of gravity relative to detector 120. Actuator 130 includes a support 131, a first arm 132 (also referred to x-ray source arm) attached to support 131 and to x-ray source 110, a second arm 134 (also referred to as x-ray detector arm) attached to support 131 and to detector 120, and an actuating system 140.

X-ray source 110 is typically an x-ray tube and detector 120 is typically a digital x-ray detector. For example, detector 120 may be a solid state radiation imager, having e.g., a cesium iodide phosphor (scintillator) on an amorphous silicon transistor-photodiode array. Other suitable detectors may include one or more charge coupled devices (CCD) or a direct digital detector which converts x-rays directly to digital signals. While detector 120 is illustrated as being flat and defining a flat image plane, other configurations of digital x-ray detectors may be suitably employed, e.g., a curved-shaped digital x-ray detector having a curved image plane.

X-ray source 110 and detector 120 are separately movable relative to each other. For example, arm 132 has a first end 211 or portion attached to x-ray source 110 and a second end 212 or portion pivotally attached to support 131 so that x-ray source 110 is rotatable about a point or axis R in the directions indicated by curved double-headed arrow C. Similarly, arm 134 has a first end 221 or portion attached to detector 120 and a second end 222 or portion pivotally attached to support 131 so that detector 120 is rotatable about axis R in the directions indicated by double-headed arrow D.

X-ray source 10 and arm 132 are suitably weighted to provide a moment on the upper portion 211 of arm 132, i.e., the portion above axis R, which moment is greater than the moment of the lower portion 212 of arm 132, i.e., the portion below axis R. Desirably, when x-ray source 110 is positioned at a first or elevated upper position 201 (as shown in FIGS. 2 and 3), arm 132 and x-ray source 110 will tend to rotate about axis R so that x-ray source 110 moves along arc C to a second or lower position 202 (as shown in phantom in FIGS. 2 and 3).

In this exemplary embodiment, actuating system 140 comprises a hydraulic system having first and second hydraulic cylinders 142 and 144, respectively, a reservoir 160, a pump 170, and valves 172 and 174. Hydraulic cylinder 142 comprises a cylinder body 141 pivotally attached to support 131, and a piston 143 pivotally attachable at an upper end to one side of arm 132 for positioning x-ray source 110 relative to detector 120. Hydraulic cylinder 144 comprises a cylinder body 145 pivotally attached to support 131, and a piston 147 pivotally attachable at an upper end to the other side of arm support 132 for positioning x-ray source 110 relative to detector 120, Reservoir 160, pump 170, and valves 172 and 174, are operably connected to hydraulic cylinders 142 and 144 so that fluid may be introduced into and removed from cylinder bodies 141 and 145 to position arm 132, and thus x-ray source 110 in an elevated position (e.g., position 201), relative to detector 120. Hydraulic cylinders 142 and 144 are suitably stabilized or maintained in a generally vertically disposed position when they are not attached to the respective sides of arm 132, or when apparatus 100 is operated to obtain standard cranial-caudal or medio-lateral oblique mammograms in which case, arm 132 and arm 134 may be suitably locked in a fixed position relative to support 131.

By way of example and not limitation, the x-ray source, the support, and the arms typically are of a type such as General Electric Medical Systems Model Senographe 2000D Digital Mammography System, and suitably modified as discussed above. It is to be appreciated by those skilled in the art that pneumatic cylinders may be suitably employed in place of the hydraulic cylinders. With pneumatic cylinders, a reservoir would not be necessary. It is also to be appreciated that various other mechanical components, e.g. ballscrew-drives, non-hydraulic systems and the like, may be used in apparatus 100 to effect the movement described above for obtaining images.

With reference to FIG. 2, the initial setup of apparatus 100 for obtaining tomosynthesis data is as follows. Desirably, x-ray detector arm 134, and thus detector 120, is disposed at a fixed angle B from vertical (shown by reference line Y in Figures); typically angle B is in the range between about 50 degrees to about 70 degrees from vertical for medio-lateral oblique views. When angle B has been selected, arm 134 is secured in place to prevent movement. Hydraulic cylinder 142 is attached to x-ray source arm 132. Pump 170 is energized to fill cylinder body 143 to elevate and position x-ray source 110 at an elevated position 201 as shown in FIG. 2, e.g., at a maximum angle in accordance with known techniques from an axis L1 extending normal to detector 120.

An object volume to be imaged 102, such as a breast of a patient, is positioned between a compression paddle 122 and detector 120, and maintained in a stationary fixed position while x-ray source 110 is moved from the elevated position to a lower position 202 (shown in phantom) during which a plurality of images are obtained. The procedure is similar for obtaining images of the patient's other breast, but instead, hydraulic cylinder 144 is connected to arm 132 and motion of the arm is between the respective upper and lower positions 201 and 202 as illustrated in FIG. 3.

In one aspect of obtaining the plurality of images, valve 172 may be opened to drain fluid from cylinder body 141 to reservoir 160 so that x-ray source 110 descends smoothly under the influence of gravity from the elevated position 201 to the lower position 202. As used herein, "smooth descent" and the like refer to the x-ray source moving between respective radiating positions without intermediate stops and in a fashion that does not involve abrupt changes in acceleration. During the descent of x-ray source 110, a plurality, desirably between eight and fifteen, images are obtained by the x-ray source emitting radiation towards the object to be imaged and the detector. For example, for a maximum angle of ±24 degrees, use of six degree intervals, positions "a" through "i" shown in FIG. 2, result in obtaining nine images. Each position at which the source emits radiation towards the object to be imaged is a respective radiating position. The image obtained at each position by the detector desirably are acquired with a low radiation dose. The total radiation dose for all of the images is desirably equivalent to, or only higher by a medically insignificant amount than the radiation dose for a standard single view mammogram.

Apparatus 100 desirably includes a processor 150 for controlling actuator system, and processing a plurality of images obtained at a plurality of positions of x-ray source 110 relative to detector 120 as further described below.

For example, a suitable inclinometer 180 having a sensitivity of about +/−0.1 degree may be attached to arm 132 and coupled to processor 150. Processor 150 typically also is interfaced with x-ray source 110 to supply a signal for energizing x-ray source 110 at the appropriate positions, e.g., positions "a–i", as x-ray source descends from the elevated position 201 to lower position 202. Advantageously, apparatus 100 includes suitable shock absorbers such as springs, or pressurized reservoirs to bring arm 132 to a gentle stop at position 202; alternatively processor 150 is programmed to slowly close valve 172 to decelerate x-ray source 110 as it approaches its position 202 at the end of the scan.

In another aspect of obtaining the plurality of images, x-ray source 110 may be moved to come to a rest or stop at each of the appropriate positions, e.g., positions "a–i", at which time (when no longer in motion) x-ray source is energized for generating an exposure. For example, processor 150 typically is interfaced with inclinometer 180 and valve 172 to control the descent of and cause x-ray source to come to a rest at each of the desired positions, as well as supply a signal for energizing x-ray source 110 while x-ray source is stopped or stationarily maintained at each of the desired positions.

From the present invention, it will be appreciated by those skilled in the art that instead of an inclinometer, a linear encoder or similar device can be attached to the hydraulic cylinder and calibrated for providing angular measurements. Similarly, the encoder can be interfaced with the computer and used to control the position of the x-ray source.

Figure 4:
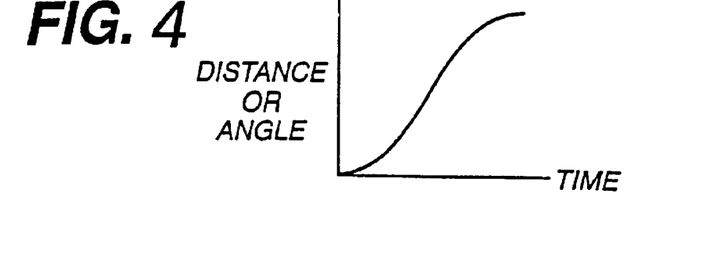
FIGS. 4–6 are partial graphical illustrations of distance or angle, velocity, and acceleration, respectively, of the motion of the x-ray source, shown in FIGS. 2 and 3, over time during a procedure for obtaining projection radiographs used for generating tomographic data.
Figure 5:
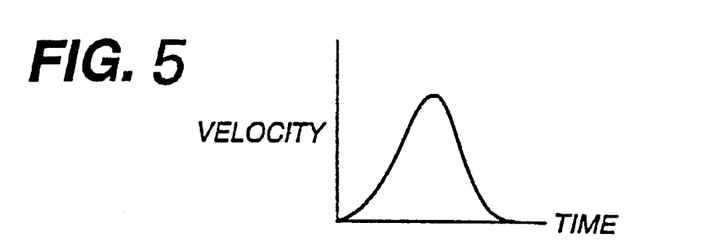
Figure 6:
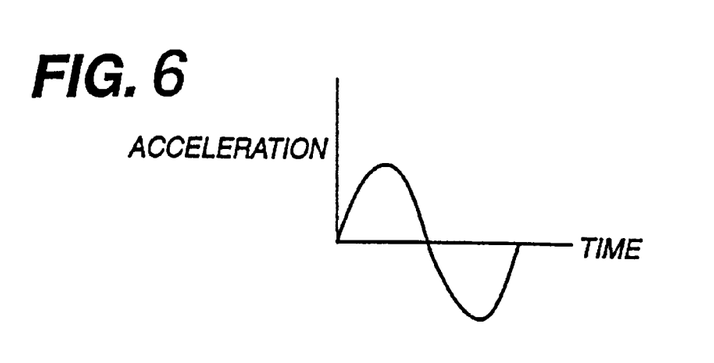

FIGS. 4–6 graphically illustrate an exemplary motion of x-ray source 110 which desirably results in a smooth transition from the upper or elevated position 201 to the lower or end position 202. FIG. 4 illustrates the change in distance or angle over time between the stop positions of the arm (e.g., positions 201 and 202). FIGS. 5 and 6 illustrate the change in velocity and acceleration, respectively, between the stop positions over time. Desirably, the accelerations and deceleration of x-ray source over time between the elevated position and the lower position is generally smooth, e.g. sinusoidal, in nature to provide the desired smoothness in motion of the arm.

Figure 7:
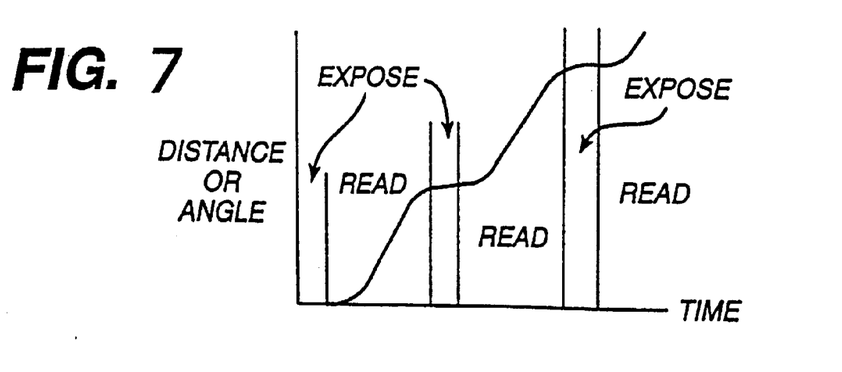
FIG. 7 is a graphical illustration similar to FIG. 4 which spans a period of time for obtaining a plurality of images; and, FIG. 8 is a schematic depicting a ray cast through a data volume in accordance with embodiments of the present invention.

Desirably, as shown in FIG. 7, the change in distance or angle between respective positions "a–i" over time for a plurality of positions results in x-ray source 110 being maintained in a fixed or stationary position at which time X-ray source is energized. The periods of time between the exposures allow the processor to read out the data from the digital detector. Advantageously, x-ray source is quickly and smoothly moved during the minimum time required for reading the detector.

In an alternative embodiment of the actuator, an intermediate pair of variable sized reservoirs may be used in the drain line from each of the hydraulic cylinders so that the pair of reservoirs are alternately filled and emptied. The volume of each reservoir is desirably configured to contain an amount of fluid to be drained or removed from the hydraulic cylinder to permit x-ray source 110 to move from one position to the next. For example, when a reservoir is filled, the x-ray source can be energized to generate an exposure. The hydraulic cylinder would then be connected to the other reservoir to continue the scan, while the first would be emptied into the lower reservoir.

The hydraulic system and motion of the x-ray source allows for the acquisition of the tomosynthesis images in approximately three to five seconds which is sufficiently rapid to make the apparatus clinically applicable. The separate projection radiographs obtained during the imaging procedure typically are processed for use by the operator by processor 150 or other readout modalities coupled to the detector.

The plurality of separate projection radiographs generated by apparatus 100 (x-ray source 110 located at positions "a–i"), after preprocessing, are shifted, scaled, and added, e.g., transformed, to reconstruct one or more planes or slices S in the object imaged that are parallel to the plane of detector 120. It is to be appreciated that one skilled in the art would select from a variety of reconstruction techniques suitable for a given imaging application. As used herein, the plurality of planes or slices are referred to as tomosynthesis data. Tomosynthesis data describes the reconstructed data whereas projection radiographs refer to the x-ray shots. Tomosynthesis allows reconstruction of "in-focus" tomographic planes or slices S at any level within the imaged object, e.g., at about 1.0 mm spacing. Typically, equally spaced slices with a slice separation of about 1 mm are employed. However, other spacings and/or irregular spacings are alternative embodiments. The values in the tomosynthesis data set ideally have an obvious functional relationship with the linear attenuation values of the corresponding structures within the imaged object. Advantageously, the invention allows a physician or radiologist to see through "structured noise" of normal breast tissue to improve detection and characterization of breast cancer.

By way of example and not limitation, the generation of tomographic planes or slices S may alternatively be obtained by the processes disclosed in U.S. Pat. No. 5,872,828 to Niklason et al., or other suitable reconstruction algorithms known in the art.

After employing the tomographic imaging methods described above, the volume of the resultant tomographic data is generally large and the content of the data generally may contain a considerable dynamic range of voxel intensity values. In embodiments of the present invention, methods are provided to enable visualization, for example for diagnosis, of tomosynthesis data having considerable data volume and content. With respect to the volume, the plurality of spaced-apart images desirably have an in-plane image resolution of 100 micron (for breast imaging) or better and image spacing resolution of 1000 micron or better. Typically, each image represents a matrix size of approximately 2304×1800 voxels. As used herein, a voxel refers to a single data point within a data volume consisting of $N_x$ by $N_y$ by $N_z$ data samples along the X, Y, and Z axes respectively. Typically, there are 10 images per cm of compressed thickness, with the compressed breast thickness typically ranging from about 4 cm to about 7 cm. Thus, tomographic imaging as described herein provides a large volume of data. With respect to the content of the data, the dynamic range of the data obtained by the techniques described above desirably utilizes 2 bytes of information (voxel intensity) to store the range difference in attenuation coefficients of imaged structures. There is a relationship between the voxel intensity value and the attenuation coefficients of the imaged structures. The output of the reconstruction technique can make this relationship either proportional or inversely proportional. For an inversely proportional relationship, the higher the attenuation coefficient of a structure within the breast, the lower its intensity value. For example, a microcalcification has voxel values lower than voxel values associated with fibrous tissues. Other functional relationships between voxel intensity values and attenuation of the imaged structures are also possible.

In an embodiment of the present invention, a method for generating a three-dimensional image of an object volume, for example a patient's breast, comprises obtaining tomosynthesis data of the object volume as described above and generating the three-dimensional image by applying a 3D visualization technique to the tomosynthesis data. 3D visualization techniques, as used herein, refer to a variety of known volume rendering techniques such as maximum, minimum, composite, surface or averaged projections made at any arbitrary view angle in accordance with known techniques.

Figure 8:
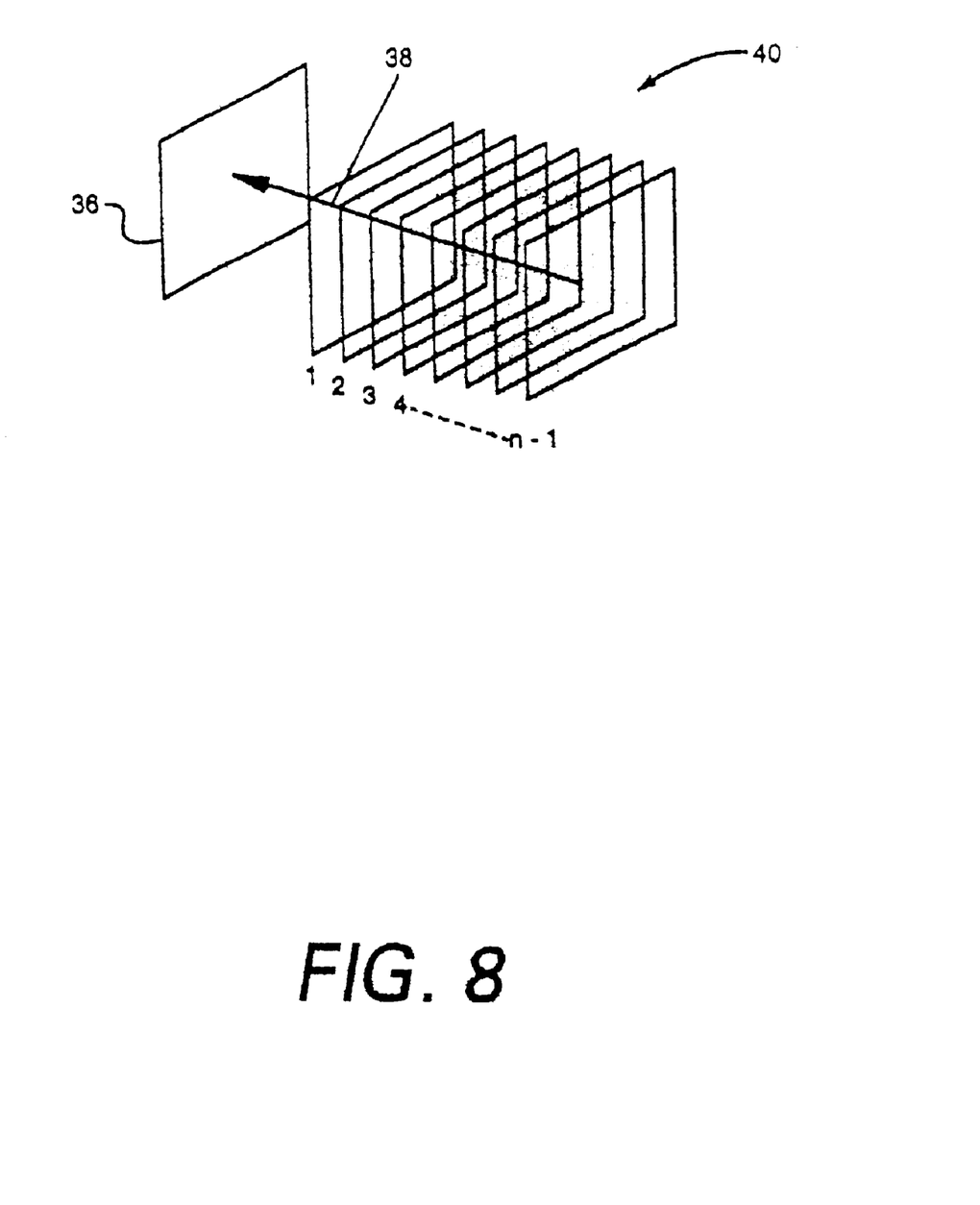

Volume rendering refers to various techniques to generate projected images onto various imaging planes in order to generate a three-dimensional rendering of the imaged object volume. The tomosynthesis data, i.e., the plurality of spaced-apart planar images, obtained by the methods described above collectively form a three-dimensional data volume representing the object volume. Referring to FIG. 8, there is shown an exemplary data volume 40 that comprises n slices numbered from 0 to (n−1). The projected images are shown as 36. In order to generate three-dimensional images from the data volume, processor 150 of FIG. 2 is adapted to transform the data volume using volume rendering techniques. In an exemplary embodiment, volume rendering is performed with maximum opacity ray casting. As used herein, opacity is defined as a measurement of transparency. In this embodiment, a ray 38 is cast through data volume 40. As ray 38 passes through each plane in data volume 40, a rendered image is formed by calculating and accumulating intensity from the intersection or ray 38 with pixels from each of the given slices of the data volume. Processor 150 iteratively performs the ray casting volume rendering in accordance with known methods. Generally the number of pixels for each of the directions in the two-dimensional slice are predetermined, e.g. number of pixels in x-direction and number of slices in y-direction, based on resolution requirements. Typically, the resolution of a final image is predetermined. However, lower resolution is often employed during interactive sessions to reduce processing time. In an embodiment of a method for generating a 3D image, a selected 3D visualization technique, is applied responsive to a user input to enable user manipulation of the image, e.g. orientation and view angle at various resolutions. In alternate embodiments, processor 150 is adapted to enable interactive sessions with the image at higher resolutions. In alternative embodiments, other volume rendering techniques such as two-dimensional or three-dimensional texture mapping, maximum intensity value projection, minimum intensity value projection or composite ray casting are selected to generate a three-dimensional image of the breast using tomosynthesis data. In alternate embodiments, surface rendering techniques may be used alone or in combination with the various volume rendering techniques. It is to be appreciated that surface rendering techniques enables the ability to readily extract regular and irregular shaped volumes of interest, an ability which is desirable in reviewing tomosynthesis data. In other words, surface rendering will be used on some geometrical objects (e.g sphere, ellipse, tube, etc). The intersection of the 3D data with these geometrical objects can lead to the reconstruction of the volume of interests with the imaged 3D volume.

In order to display and manipulate the three-dimensional rendered image for diagnosis purposes, two main parameters are desirably set for each voxel in the ray casting technique colors and opacity. Typically, there are two piecewise linear transfer functions that are used to set these parameters. One transfer function is used to set for colors (e.g. red, green and blue or RGB) and the other transfer function is used to set for opacity. Since, generally the rendered 3D image is shown in gray for most radiologists, all of the red, green and blue values are typically the same.

In the field of visualization, it is typical to refer to color monitors with RGBA colors (Red, Green, Blue, and Alpha). These colors refer to the electronic guns in the monitors. If only the red gun is turned on then the pixels on the screen would appear red, if the red and the green guns are turned on then the pixels would appear yellow, and if all of the guns are turned on then the pixels would appear white. The strength of the intensity of the guns generates different levels of shading. When the intensities of all the electronic guns are changed by the same amount and thus the same value, the pixels would have different gray scale values. Typically, radiologists have been trained to look at films which have gray scale values, and they prefer to look at digital images also in gray scale values, but this could change if the radiologists were to get trained on color images. The alpha value (opacity) refers to blending two planes. One plane refers to the colors generated from the screen and the other is opacity plane or alpha plane. Therefore, each pixel has an alpha value associated with it. Generally, in a monotonically increasing transfer function a value of 1 means the pixel on the screen is very opaque and a value of 0 means the pixel is very transparent.

Each transfer function maps the fully dynamic range of the original data into either 8 or more bits depending on the depth of the available display. Although the full dynamic range of the data is typically 15 bits, the necessary dynamic range to render a volume of interest (VOI) without a loss of depth of information requires generally a lesser number of bits. For instance, viewing only micro-calcification with full depth resolution requires a lesser number of bits than viewing both micro-calcifications and masses, cysts, or other lesions or soft tissue structures with full depth resolution. Thus, high resolution visualization of breast structures is possible utilizing embodiments of the present invention.

Note that, micro-calcifications have a distribution of intensity values that are more separated than the soft tissue structure intensity value distribution. Therefore, to map or scale the 15 bits depth resolution (all of the intensity values including the distributions for both micro-calcifications and soft tissue structures) to 8 bit depth resolution, there would be a loss of depth information. However, one intensity value distribution (e.g. soft tissue structures) covers fewer than 15 bits, and therefore scaling one intensity value distribution to a 8 bits display leads to a lesser loss of depth information for that specific distribution.

Processor 150 is typically a digital computer that is programmed to process image signals received from detector 120 during the x-ray procedure, to preprocess said images, and to generate (i.e., reconstruct) tomosynthesis data. In an embodiment of present invention, processor 150 is further adapted to generate 3D images based on tomosynthesis data, as described in greater detail above. As used herein, "adapted to", "configured" and the like refer to operation capabilities of electrical elements such as analog or digital computers or application specific devices (such as an application specific integrated circuit (ASIC)) that are programmed to perform a sequel of instructions to provide an output in response to given input signals. An exemplary processor 150 may include a suitable computer (e.g., SPARC 20 workstation from Sun Microsystems, PENTIUM based computer, etc.) having a hard, drive, input devices such as a keyboard, a mouse, magnetic storage media (e.g., tape cartridges or disks), optical storage media (e.g., CD-ROMs), and output devices such as a display and a printer. Suitable programming to perform the processing steps, as explained in greater detail above, is installed or embedded in processor 150.

In a further embodiment, a system for generating three-dimensional images of an object volume is provided. The system comprises an imaging device and an image processing device. The imaging device, as described above, irradiates the volume with radiation at a plurality of radiating positions and further generates a plurality of spaced-apart planar images through the object volume by performing a suitable reconstruction algorithm based on projection radiographs derived by detecting radiation at the plurality of radiating positions. The image processing device, such as processor 150 of FIG. 2, generates a three-dimensional image of the object volume based on the spaced-apart planar images. The 3D image is available for display to a user of the system (a display device is not shown). In further embodiments, the image processing device is adapted to respond interactively to inputs from a user of the system for a desired display format. For example, a user such as a radiologist may select a specific region or view angle of the rendered 3D volume or, alternatively, may want to review the 3D image based on parameters such as intensity. It is to be appreciated that with suitable programming processor 150 is adapted to respond to user input for a desired display of the rendered 3D image. In another further embodiment, processor 150 is adapted to provide an animated video display of the rendered 3D image.

From the present description, it will be appreciated the apparatus may be configured to image a variety of objects, and is not limited to breast imaging.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

What is claimed is:

1. A method for generating at least one three-dimensional image of an object volume, the method comprising:
   generating the at least one three-dimensional image by applying a selected three-dimensional (3D) visualization technique responsive to a user input for a desired display format to tomosynthesis data obtained for the object volume;
   wherein the selected 3D visualization technique comprises performing at least one of opacity ray casting, two-dimensional or three-dimensional texture mapping, maximum intensity value projection, minimum intensity value projection, composite ray casting and surface rendering to the tomosynthesis data.

2. The method for claim 1 wherein the generating step comprises rendering a three-dimensional image from the plurality of spaced-apart planar images.

3. The method of claim 1 wherein the display format is selected from at least one of a display based on view angle or selected region of the three-dimensional volume, a display based on selected parameters and an animated video.

4. A method for generating at least one three-dimensional image of an object volume, the method comprising:
   obtaining tomosynthesis data of the object volume; and,
   generating the at least one three-dimensional image by applying a selected three-dimensional (3D) visualization technique responsive to a user input for a desired display format to the tomosynthesis data;
   wherein the 3D visualization technique comprises performing at least one of opacity ray casting, two-dimensional or three-dimensional texture mapping, maximum intensity value projection, minimum intensity value projection, composite ray casting and surface rendering to the tomosynthesis data.

5. The method of claim 4 wherein the tomosynthesis data comprises a plurality of spaced-apart planar images through the object volume generated from a plurality of projection radiographs which are derived by detecting radiation passing through the object at the plurality of radiating positions with the radiation detector.

6. The method of claim 5 wherein the generating step comprises rendering a three-dimensional image from the plurality of spaced-apart planar images.

7. The method of claim 4 wherein the display format is selected from at least one of a display based on view angle or selected region of the three-dimensional volume, a display based on selected parameters and an animated video.

8. A method for generating at least one three-dimensional (3D) image of an object volume, said method comprising:

positioning a radiation source in an elevated position with the object volume disposed between the radiation source and a radiation detector;

irradiating the object volume with radiation at a plurality of radiating positions as the radiation source is allowed to move under the influence of gravity from an elevated position to a lower position;

generating a plurality of spaced-apart planar images through the object volume from a plurality of projection radiographs which are derived by detecting radiation passing through the object at the plurality of radiating positions with the radiation detector, the plurality of spaced-apart planar images collectively forming a data volume;

applying a selected three-dimensional (3D) visualization technique to the data volume to generate the at least one three-dimensional image of the object volume.

9. The method of claim 8 wherein the 3D visualization technique comprises performing at least one of opacity ray casting, two-dimensional or three-dimensional texture mapping, maximum intensity value projection, minimum intensity value projection, composite ray casting and surface rendering to the data volume.

10. A system for generating at least one three-dimensional (3D) image of an object volume, comprising:

an imaging device for irradiating the volume with radiation at a plurality of radiating positions and for generating a plurality of spaced-apart planar images through the object volume from a plurality of projection radiographs which are derived by detecting radiation at the plurality of radiating positions; and, an image processing device coupled to the imaging device for generating at least one three-dimensional image of the object volume based on the spaced-apart planar images by applying a selected three-dimensional (3D) visualization technique responsive to a user input for a desired display format to tomosynthesis data obtained for the object volume;

wherein the selected 3D visualization technique comprises performing at least one of opacity ray casting, two-dimensional or three-dimensional texture mapping, maximum intensity value projection, minimum intensity value projection, composite ray casting and surface rendering to the tomosynthesis data.

11. The system of claim 10 wherein the image processing device is adapted to respond to a user input for a desired display format.

12. The system of claim 11 wherein the desired display format is selected from at least one of display based on view angle or selected region of the three-dimensional volume, display based on selected parameters and animated video display.

13. The system of claim 10 wherein the imaging device is adapted to image a patient's breasts.

* * * * *